US010590402B2

(12) United States Patent
Hartmann et al.

(10) Patent No.: US 10,590,402 B2
(45) Date of Patent: Mar. 17, 2020

(54) USE OF ENZYMES WITH A WIDE PH ACTIVITY RANGE AS MEDICAMENTS FOR PROMOTING DIGESTION

(71) Applicant: CILIAN AG, Münster (DE)

(72) Inventors: Marcus Wolf William Hartmann, Münster (DE); Ingo Aldag, Münster (DE)

(73) Assignee: CILIAN AG, Münster (DE)

( * ) Notice: Subject to any disclaimer, the term of this patent is extended or adjusted under 35 U.S.C. 154(b) by 42 days.

(21) Appl. No.: 15/545,583

(22) PCT Filed: Jan. 22, 2016

(86) PCT No.: PCT/EP2016/051341
§ 371 (c)(1),
(2) Date: Nov. 3, 2017

(87) PCT Pub. No.: WO2016/116600
PCT Pub. Date: Jul. 28, 2016

(65) Prior Publication Data
US 2018/0073001 A1  Mar. 15, 2018

(30) Foreign Application Priority Data

Jan. 22, 2015  (GB) .................................. 1501081.2

(51) Int. Cl.
*C12N 9/20* (2006.01)
*A61K 38/46* (2006.01)

(52) U.S. Cl.
CPC .............. *C12N 9/20* (2013.01); *A61K 38/465* (2013.01); *C12Y 301/00* (2013.01)

(58) Field of Classification Search
None
See application file for complete search history.

(56) References Cited

U.S. PATENT DOCUMENTS

| | | | |
|---|---|---|---|
| 4,695,457 | A | 9/1987 | Hellgren et al. |
| 5,807,726 | A | 9/1998 | Blanchard et al. |
| 6,051,220 | A | 4/2000 | Scharpe |
| 7,718,169 | B2 | 5/2010 | Margolin et al. |
| 2001/0046493 | A1 | 11/2001 | Margolin |
| 2002/0142399 | A1 | 10/2002 | Mahadik et al. |
| 2004/0057944 | A1 | 3/2004 | Galle et al. |
| 2008/0292610 | A1* | 11/2008 | Hartmann .............. A61K 38/43 424/94.63 |
| 2009/0133322 | A1 | 5/2009 | Basheer et al. |

FOREIGN PATENT DOCUMENTS

| | | |
|---|---|---|
| CN | 103266094 A | 8/2013 |
| CN | 104031899 A | 9/2014 |
| WO | 0046381 A1 | 8/2000 |
| WO | 0058483 A2 | 10/2000 |
| WO | 2007006812 A1 | 1/2007 |
| WO | 2007053619 A2 | 5/2007 |

OTHER PUBLICATIONS

Arai et al., "Intracellular phospholipase activities of Tetrahymena pyriformis", Journal of Biochemistry 1985, vol. 97, pp. 1525-1532 (Year: 1985).*
Alter GM, Leussing DL, Neurath H, Vallee BL (1977): Kinetic properties of carboxypeptidase B in solutions and crystals. Biochemistry. Aug. 9;16(16):3663-8.
Tondravi, MM; Yao,M-C (1986): Transformation of Tetrahymena thermophila by microinjection of ribosomal RNA genes. PNAS 83, 4369-4373.
Gaertig,J; Gorovsky,MA (1992): Efficient mass transformation of Tetrahymena thermophila by electroporation of conjugants. PNAS 89, 9196-9200.
Cassidy-Hanley, D.; Bowen, J.; Lee, J.; Cole, E.; VerPlank, L.; Gaertig, J.; Gorovsky, M. & Bruns, P. Germline and somatic transformation of mating Tetrahymena thermophila by particle bombardment. Genetics, 1997 , 146 , 135-47.
Nixon M, Chang SH. A simple and sensitive colorimetric method for the determination of long-chain free fatty acids in subcellular organelles. Anal Biochem. Sep. 1, 1979;97(2): 403-409.
Weide, T.; Herrmann, L.; Bockau, U.; Niebur, N.; Aldag, I.; Laroy, W.; Contreras, R.; Tiedtke, A. & Hartmann, M. W. W.: Secretion of functional human enzymes by Tetrahymena thermophila. BMC Biotechnol, vol. 6, pp. 19, 2006.
Margolin, A. L. (1995) Novel crystalline catalysts. Trends in Biotechnology 14 (7): 223-230).
Gargouri, Y.; Pieroni, G.; Lowe, P.; Sarda, L. & Verger, R.: Human gastric lipase. The effect of amphiphiles. In: Eur J Biochem 156 (1986), Nr. 2, S. 305-10.
Jette J.F. & Ziomek E. (1994): Determination of lipase activity by a rhodamine-triglyceride-agarose assay. Anal. Biochem 219, 256-260.
Carome M. Wolfe S. Testimony to the FDA Gastrointestinal Drug Advisory Committee regarding liprotamase—risk: benefit assessment; ethics of further clinical trials. Washington DC: Public Citizen Research Group. Jan. 12, 2011).
Zhong, Q., GU, Gu, Z. and Glatz, C. E. (2006) Extraction of recombinant dog gastric lipase from transgenic corn seed. J. Agric. Food Chem. 54: 8086-8092).
Carriere, F., Moreau, H., Raphel, V., Laugier, R., Benicourt, C., Junien, J.-L. and Verger, R., 1991) Purification and biochemical characterization of dog gastric lipase. Eur. J. Biochem. 202: 75-83.
United States Pharmacopeia 23, NF18 1095, pp. 1150-1151, (1995).
Fallingborg J, Dan Med Bull. Jun. 1999;46(3):183-96.

(Continued)

*Primary Examiner* — Michelle F. Paguio Frising
(74) *Attorney, Agent, or Firm* — Baker Botts L.L.P.

(57) ABSTRACT

Disclosed is a combination of two or more lipase enzymes, and its use for treating a lipid digestion deficiency and/or a digestive disorder. At least one lipase enzyme has a pH optimum at an acidic pH value, while at least one other lipase enzyme has a pH optimum at an alkalic pH value.

7 Claims, 5 Drawing Sheets
Specification includes a Sequence Listing.

(56) References Cited

OTHER PUBLICATIONS

Giuliano CA1, Dehoorne-Smith ML, Kale-Pradhan PB (2011) Pancreatic enzyme products: digesting the changes. Ann Pharmacother. 45(5):658-66.
Cantor M et al,, Cheese: Chemistry, Physics and Microbiology Major Cheese Groups, Jan. 1, 2004 Elsevier, London.
Mase T et al., Purification and Characterization of Penicillium roqueforti IAM 7268 Lipase, Bioscience Biotechnology Biochemistry, Jan. 1, 1995, Japan Society for Bioscience, Biotechnology, and Agrochemistry, Tokyo, Japan, vol. 59,Nr:2,pp. 329-330, (2014).
Akio Sugihara A, et al., "Separation and characterization of . . . " J. Biochem., vol. 107, 1990, pp. 426-430 see esp. Abstract, Figure 5.
Gargouri, Y. et al., "Gastric lipases . . . ", Biochim. Biophys. Acta, vol. 1006, 1989, pp. 255-271 see esp. p. 259.
Search report of the UKIPO regarding the priority application (5 pages), (Oct. 26, 2015).
International Search Report of the underlying PCT application (4 pages), (May 27, 2016).
Written Opinion of the ISA with regard to the underlying PCT application (5 pages).

\* cited by examiner

SEQUENCE LISTING

```
<160> NUMBER OF SEQ ID NOS: 6

<210> SEQ ID NO 1
<211> LENGTH: 867
<212> TYPE: DNA
<213> ORGANISM: Artificial Sequence
<220> FEATURE:
<223> OTHER INFORMATION: synthetic construct; sequence of lipase 10

<400> SEQUENCE: 1
atgaaattgt aattgcttct attggtttgc ttgtcatttg ctgcctgcta atcatttact    60
tatacttaat cacttgctta agacttagct ggtttctctc ttgcttctta ctgtaatcct   120
aaatctatag aacaatggaa ttgtggatgt gcttgtgata aaaaccctta aggacttcga   180
aatgttacta tcttatttaa ctctactcta taagctagtg gatatttagg ctactccact   240
catcatgatg caattgttgt tgtattcaga ggaacagtac cttggttaat cgaaaattgg   300
attgctgact taaacacctt caagacttag tacccactct gccaaaactg ttatgtccat   360
taaggctttt ataaccagtt caaataattg aaatctcagc ttgttactag ctttacttca   420
cttcgttaac tatatcctaa tgcaaaagta tttgttacag gacattctct tggtgctgca   480
atgagtgctc actcaatacc agtaatttac taattaaatg gaaataaacc tattgatgct   540
ttttacaatt atggttgtcc tagagtaggt gactaaaactt atgcaaactg gtttaacagt   600
taaaattttg ccttagaata tggtagaatt aataatgctg ctgatccagt tcctcattta   660
cctcctcttc tttacccatt ttcatttttc cactacaacc atgaaatatt ctatccttct   720
tttgttcttt ttggaaacta acataactaa tgttaaaacg cggaaacaat atttggtgca   780
```

```
gatggagtaa taatagcagc taatgttcta gaccatctaa cttatttggg atgggattgg      840
tctggttcta tattaacttg ctaatga                                         867

<210> SEQ ID NO 2
<211> LENGTH: 986
<212> TYPE: DNA
<213> ORGANISM: Artificial Sequence
<220> FEATURE:
<223> OTHER INFORMATION: synthetic construct; sequence of lipase 11

<400> SEQUENCE: 2
atgaaatcaa ttttttatt aattatttcc ttgcttttag cttcttgctc atagttttaa       60
tataatgaaa cacttgccta agacttagct ggattttctc ttgcttctta ctgtaatcct     120
aaatatttat aataatggaa ttgtggctct gcttgtaaaa aaacccaaa tggtcttaca      180 gatttctctt atttgtataa caagacttta aaggcaagtg gatatatagg ctattctgct     240
catcatgatg ctattatagt tgtctttaga ggaactgtcc cttggttgat ctaaaattgg     300
attgcagatt taaacactat caaaatttaa tatccttctc gtgaaaattg ttatgttcat    360
aaaggtttct ataaatagtt caattaatta aaatcttaac ttatttaaag ctttacagaa     420
attcgttaaa aatatccttc atcaaaaata tttgtcactg gacattctct tggtgcagct     480
atgagttttc attcaatgcc tattattttt gaattaaatg gaaataagcc tattgatgct     540
ttctataatt atggttcccc aagagttggt aacgaagcat atgcaacttg gtttaattta    600
caaaattttg ctttataata tggcagaata ataatgcag cagatcctgt tcctcattta    660
cctcctattc ttttcccttt ctaatttttat catactaatc atgaaatatt ttatacttca   720
tttattgaag atggtaacaa atatgagtaa tgcttagatg cagaacacaa attatgtgca    780
aatagtaaga ttattgctgc aagcgttcgt gaccatctta gttatttggg ctggaattgg    840
gctacttcta ttttaacttg ccaatgaatt aaaaaattaa tttatcaaac aaaaacatta    900
actaaaatta ttttatctg tttaaatttg ttttaaaaca tttatatttt attttaatat     960
ttactacttt ttagaataaa atatct                                         986

<210> SEQ ID NO 3
<211> LENGTH: 1267
<212> TYPE: DNA
<213> ORGANISM: Artificial Sequence
<220> FEATURE:
<223> OTHER INFORMATION: synthetic construct; sequence of lipase 14

<400> SEQUENCE: 3
atgaacaaat tgcaagttct tttcattgca gctatagttt gcacaattgg atccactgtt      60
tatttactca ataagagctc ttcagatgtc caagagtctt aactgacttt cccctatgat     120
gaaaatttag ctgaaaattt agctggattt tctatggctt cttattgtaa agcttctaaa     180
attgaaaact ggaattgcgg tgcttcttgc aaaaaaaatc ccgaaggact ttaagatgtc     240
tacattatga aaaataaaac tatgaacgct gctggtttct tagcatattc tcctgctcat     300
gatgctatag tagttgtatt tagaggaact gtcccctggt tgatcaagaa ttggattagt    360
gacattaaca ctgtcaaaac aaaatactct agatgcgaaa aatgctatgt tcatttgggc    420
ttcttcaatg ccttcaagga attgtaagat taaattctta ctgagttccc taaacttaag    480
gccaaatatc cttattcaaa ggtaatttaa cacaaaatat acatatatct ctttataaat    540
aattcatgct atcatatgtt tttctttaga ttattgtgta tttcaaaagc atcaccttag    600
cctttaaata ttgattaagg aaatattaaa tgatttgtaa aatcaattgc aagaatataa    660
```

-continued

```
attactctaa attaaatcga cgtatgaatc gaatacccaa ctaattatag gcattaataa      720
attttggaaa attatttgtt ttctcaattt tcaatatgaa atttagctt aacttatttg       780 gcttttaata tttattccac ttttacatc ttattcatca attatattta ttttaaactc       840
atttaaaaat aaataggttt ttgttacagg tcattccctt ggtgctgcaa tgagtactca      900
cgctgttcct gtcatttatg aactcaatgg aaataagcct atcgatgcat tctataattt      960
tggttcccct agggttggtg atgaaaatta ccactaatgg ttcgatagct aaaattttac     1020
tctttaatat ggtagaatta accacagagc tgatccagtt cctcatttac cccctaatta    1080
ctctcctttc actttactc atattgatca tgaagttttc tattaaacat ttaagaaacc      1140
ttatacataa tgtattgaaa ctgaaagtct tgaatgtgct gatggtataa aaattccctt    1200
agatattcct gaccatcttt cttactttgg ttgggattgg gccactgaca tcttagcttg    1260
ctaatga                                                               1267
```

<210> SEQ ID NO 4
<211> LENGTH: 288
<212> TYPE: PRT
<213> ORGANISM: Artificial Sequence
<220> FEATURE:
<223> OTHER INFORMATION: synthetic construct; sequence of lipase 10

<400> SEQUENCE: 4

```
Met Lys Leu Gln Leu Leu Leu Val Cys Leu Ser Phe Ala Ala Cys
1               5                   10                  15

Gln Ser Phe Thr Tyr Thr Gln Ser Leu Ala Gln Asp Leu Ala Gly Phe
            20                  25                  30

Ser Leu Ala Ser Tyr Cys Asn Pro Lys Ser Ile Glu Gln Trp Asn Cys
        35                  40                  45

Gly Cys Ala Cys Asp Lys Asn Pro Gln Gly Leu Arg Asn Val Thr Ile
    50                  55                  60

Leu Phe Asn Ser Thr Leu Gln Ala Ser Gly Tyr Leu Gly Tyr Ser Thr
65                  70                  75                  80

His His Asp Ala Ile Val Val Phe Arg Gly Thr Val Pro Trp Leu
                85                  90                  95

Ile Glu Asn Trp Ile Ala Asp Leu Asn Thr Phe Lys Thr Gln Tyr Pro
            100                 105                 110

Leu Cys Gln Asn Cys Tyr Val His Gln Gly Phe Tyr Asn Gln Phe Lys
        115                 120                 125

Gln Leu Lys Ser Gln Leu Val Thr Ser Phe Thr Ser Leu Arg Gln Leu
    130                 135                 140

Tyr Pro Asn Ala Lys Val Phe Val Thr Gly His Ser Leu Gly Ala Ala
145                 150                 155                 160

Met Ser Ala His Ser Ile Pro Val Ile Tyr Gln Leu Asn Gly Asn Lys
                165                 170                 175

Pro Ile Asp Ala Phe Tyr Asn Tyr Gly Cys Pro Arg Val Gly Asp Gln
            180                 185                 190

Thr Tyr Ala Asn Trp Phe Asn Ser Gln Asn Phe Ala Leu Glu Tyr Gly
        195                 200                 205

Arg Ile Asn Asn Ala Ala Asp Pro Val Pro His Leu Pro Pro Leu Leu
    210                 215                 220

Tyr Pro Phe Ser Phe His Tyr Asn His Glu Ile Phe Tyr Pro Ser
225                 230                 235                 240

Phe Val Leu Phe Gly Asn Gln His Asn Gln Cys Gln Asn Ala Glu Thr
```

```
                        245                 250                 255
Ile Phe Gly Ala Asp Gly Val Ile Ile Ala Ala Asn Val Leu Asp His
                260                 265                 270
Leu Thr Tyr Phe Gly Trp Asp Trp Ser Gly Ser Ile Leu Thr Cys Gln
            275                 280                 285

<210> SEQ ID NO 5
<211> LENGTH: 288
<212> TYPE: PRT
<213> ORGANISM: Artificial Sequence
<220> FEATURE:
<223> OTHER INFORMATION: synthetic construct; sequence of lipase 11

<400> SEQUENCE: 5

Met Lys Ser Ile Phe Leu Leu Ile Ile Ser Leu Leu Leu Ala Ser Cys
1               5                   10                  15

Ser Gln Phe Gln Tyr Asn Glu Thr Leu Ala Gln Asp Leu Ala Gly Phe
            20                  25                  30

Ser Leu Ala Ser Tyr Cys Asn Pro Lys Tyr Leu Gln Gln Trp Asn Cys
        35                  40                  45

Gly Ser Ala Cys Lys Lys Asn Pro Asn Gly Leu Thr Asp Phe Ser Tyr
    50                  55                  60

Leu Tyr Asn Lys Thr Leu Lys Ala Ser Gly Tyr Ile Gly Tyr Ser Ala
65                  70                  75                  80

His His Asp Ala Ile Ile Val Val Phe Arg Gly Thr Val Pro Trp Leu
                85                  90                  95

Ile Gln Asn Trp Ile Ala Asp Leu Asn Thr Ile Lys Ile Gln Tyr Pro
            100                 105                 110

Phe Cys Glu Asn Cys Tyr Val His Lys Gly Phe Tyr Lys Gln Phe Asn
        115                 120                 125

Gln Leu Lys Ser Gln Leu Ile Gln Ser Phe Thr Glu Ile Arg Gln Lys
    130                 135                 140

Tyr Pro Ser Ser Lys Ile Phe Val Thr Gly His Ser Leu Gly Ala Ala
145                 150                 155                 160

Met Ser Phe His Ser Met Pro Ile Ile Phe Glu Leu Asn Gly Asn Lys
                165                 170                 175

Pro Ile Asp Ala Phe Tyr Asn Tyr Gly Ser Pro Arg Val Gly Asn Glu
            180                 185                 190

Ala Tyr Ala Thr Trp Phe Asn Leu Gln Asn Phe Ala Leu Gln Tyr Gly
        195                 200                 205

Arg Ile Asn Asn Ala Ala Asp Pro Val Pro His Leu Pro Pro Ile Leu
    210                 215                 220

Phe Pro Phe Gln Phe Tyr His Thr Asn His Glu Ile Phe Tyr Thr Ser
225                 230                 235                 240

Phe Ile Glu Asp Gly Asn Lys Tyr Glu Gln Cys Leu Asp Ala Glu His
                245                 250                 255

Lys Leu Cys Ala Asn Ser Lys Ile Ile Ala Ala Ser Val Arg Asp His
            260                 265                 270

Leu Ser Tyr Phe Gly Trp Asn Trp Ala Thr Ser Ile Leu Thr Cys Gln
        275                 280                 285

<210> SEQ ID NO 6
<211> LENGTH: 303
<212> TYPE: PRT
<213> ORGANISM: Artificial Sequence
<220> FEATURE:
<223> OTHER INFORMATION: synthetic construct; sequence of lipase 14
```

<400> SEQUENCE: 6

```
Met Asn Lys Leu Gln Val Leu Phe Ile Ala Ala Ile Val Cys Thr Ile
1               5                   10                  15

Gly Ser Thr Val Tyr Leu Leu Asn Lys Ser Ser Ser Asp Val Gln Glu
            20                  25                  30

Ser Gln Leu Thr Phe Pro Tyr Asp Glu Asn Leu Ala Glu Asn Leu Ala
        35                  40                  45

Gly Phe Ser Met Ala Ser Tyr Cys Lys Ala Ser Lys Ile Glu Asn Trp
50                      55                  60

Asn Cys Gly Ala Ser Cys Lys Lys Asn Pro Glu Gly Leu Gln Asp Val
65                  70                  75                  80

Tyr Ile Met Lys Asn Lys Thr Met Asn Ala Ala Gly Phe Leu Ala Tyr
                85                  90                  95

Ser Pro Ala His Asp Ala Ile Val Val Val Phe Arg Gly Thr Val Pro
                100                 105                 110

Trp Leu Ile Lys Asn Trp Ile Ser Asp Ile Asn Thr Val Lys Thr Lys
            115                 120                 125

Tyr Ser Arg Cys Glu Lys Cys Tyr Val His Leu Gly Phe Phe Asn Ala
130                 135                 140

Phe Lys Glu Leu Gln Asp Gln Ile Leu Thr Glu Phe Pro Lys Leu Lys
145                 150                 155                 160

Ala Lys Tyr Pro Tyr Ser Lys Val Phe Val Thr Gly His Ser Leu Gly
            165                 170                 175

Ala Ala Met Ser Thr His Ala Val Pro Val Ile Tyr Glu Leu Asn Gly
            180                 185                 190

Asn Lys Pro Ile Asp Ala Phe Tyr Asn Phe Gly Ser Pro Arg Val Gly
            195                 200                 205

Asp Glu Asn Tyr His Gln Trp Phe Asp Ser Gln Asn Phe Thr Leu Gln
            210                 215                 220

Tyr Gly Arg Ile Asn His Arg Ala Asp Pro Val Pro His Leu Pro Pro
225                 230                 235                 240

Asn Tyr Ser Pro Phe Thr Phe Thr His Ile Asp His Glu Val Phe Tyr
                245                 250                 255

Gln Thr Phe Lys Lys Pro Tyr Thr Gln Cys Ile Glu Thr Glu Ser Leu
                260                 265                 270

Glu Cys Ala Asp Gly Ile Lys Ile Pro Leu Asp Ile Pro Asp His Leu
            275                 280                 285

Ser Tyr Phe Gly Trp Asp Trp Ala Thr Asp Ile Leu Ala Cys Gln
            290                 295                 300
```

USE OF ENZYMES WITH A WIDE PH ACTIVITY RANGE AS MEDICAMENTS FOR PROMOTING DIGESTION

CROSS REFERENCE TO RELATED APPLICATIONS

This application claims benefit of and priority under 35 U.S.C. § 371 of PCT/EP2016/051341, filed Jan. 22, 2016, which claims the benefit under 35 U.S.C. § 119(e) of Great Britain Application No. 1501081.2, filed Jan. 22, 2015, which are incorporated herein by reference in their entirety.

REFERENCE TO SEQUENCE LISTING

The Sequence Listing submitted Nov. 2, 2017 as a text file named "13318_0027U1_Sequence_Listing.txt," created on Sep. 6, 2017, and having a size of 12,828 bytes is hereby incorporated by reference pursuant to 37 C.F.R. § 1.52(e)(5).

FIELD OF THE INVENTION

The present invention relates to a medicament containing homologous expressed enzymes from ciliates for treating digestive disorders.

BACKGROUND

Digestive disorders play an increasingly greater role in the general medical and internal medical practice. Such digestive disorders are in many cases the consequence of a more or less pronounced deficiency in so-called pancreatic enzymes. In a healthy state, these enzymes are synthesized in the pancreas by highly specialized cells, the so-called acinic cells, and secreted by exocytosis through juice glands and the main pancreatic duct into the duodenum. The daily amount of pancreatic secretion is about 2 liters. In addition to fat digesting lipase, the pancreatic secretion also contains enzymes for the digestion of proteins (trypsin, chymotrypsin and carboxypeptidases) and carbohydrates ($\alpha$-amylase). The secretion of pancreatic enzymes is exactly controlled by endogenous control mechanisms by means of hormones, such as gastrin, secretin and pancreozymin. This control system can be disturbed by a large number of causes to result in a reduction of pancreatic enzyme secretion or in a complete subsiding of the exocrine pancreatic function. This in turn causes that the chyme is not digested in the small intestine, and a digestive disorder occurs. This disease of the digestive tract, which is also referred to as exocrine pancreatic insufficiency (EPI), can have different causes. In addition to dyspepsia caused by medicaments, chronic atrophic gastritis and chronic pancreatitis, frequently caused by alcohol consumption, disorders caused by surgery (e.g., Billroth I and II, vagotomy, pancreas resection) and cystic fibrosis are etiologic factors of pancreatic insufficiency. At any rate, chronic digestive disorders are of considerable social-medical and thus economic importance, because the symptoms frequently cause the patients to be nondescript and have a shortened expectation of life.

Pancreatogenic digestive disorders and especially EPI cause a lot of complaints in the patients, such as diarrhea, mass stools, sensations of repletion, upper abdominal complaints, weight loss etc.

Irrespective of the causes and the manifestation of pancreatogenic digestive disorders or EPI to avoid malnutrition related morbidity and mortality, it is pivotal to commence a substitution therapy with enzymes as soon as EPI is diagnosed. This means that the lacking enzymes, predominantly lipase, protease and amylase, but also other enzymes, must be supplied externally. In the therapy, the enzymes are taken in orally by the patient mostly in the middle of the meal and go through the stomach and arrive in the small intestine, where they perform digestion of the chyme and thus adopt the function of the lacking endogenous pancreatic enzymes. The preparations employed must contain a sufficient amount of enzymes. In addition, the enzymes must be provided in an enteric formulation, have a small particle size and be completely bioavailable in the digestive tract.

For treating digestive disorders based on the lacking of pancreatic enzymes often pancreatic enzyme replacement therapy (PERT) based on the substitution/replacement of the leading enzyme lipase and the protease, is used. For PERT a wide variety of enzyme preparations are already on the market. These are partly based on pancreatic enzymes from pigs, such as the preparations Combizym®, Festal®, Pankreon®, Kreon®, Panzytrat®, Meteozym® or Enzym-Lefax N® Preparations containing pancreatic enzymes, so called pancreatic enzyme products or PEPs, are mostly obtained from pigs from slaughter, for example, pancreas, of pigs. The final product of the preparation process is pancreatin. PEPs are composed of porcine lipase, amylase, and protease and are used in patients with EPI secondary to cystic fibrosis, chronic pancreatitis, and pancreatectomy.

In 1938, PEPs were exempted from the Food, Drug, and Cosmetic Act of 1938 and never underwent a formal Food and Drug Administration (FDA) review process (Giuliano C A L Dehoome-Smith M L, Kale-Pradhan P B (2011) Pancreatic enzyme products: digesting the changes. Ann Pharmacother. 45(5):658-66.

PEPs from pig origin cannot be employed with patients suffering from digestive disorders who have a pig protein allergy. In addition, pigs are considered a natural reservoir of human-pathogenic influenza viruses and a vast number of viruses from porcine origin, so that contamination of pancreatin with such viruses cannot be ruled out. In other words, pancreatic tissue, which would present slaughter waste, if not further processed, can exhibit a high degree of viral contamination. In consequence based on its natural origin, the pancreatic tissue, pancreatin and PEP also can be contaminated with viruses from porcine origin. It has to be emphasized that the International Conference on Harmonisation of Technical Requirements for Registration of Pharmaceuticals for Human Use (ICH) sets a very high standard in its guideline ICH Topic Q 5 A (R1) and demands as the best reasonable assurance that the product is free of virus contamination. The Center for Drug Evaluation and Research (CDER) of the US FDA already requested intensive risk mitigation strategies for lipase containing PEPs like Creon.

This, because there is a risk for contamination of PEPs with Porcine Parvovirus and Porcine Circovirus as well as significant number of swine viruses that are known human pathogens.

Unfortunately, neither manufacturer thus far has found any viral inactivation method that can successfully demonstrate acceptable virus clearances of PEP without also degrading or reducing the pancreatic enzymes, particularly lipase, to unacceptable levels. Due to further limitations associated with analytical testing of such a complex biological material, like pancreatin, it will be difficult to determine what degradants may be introduced into the product as a result of any added viral clearance steps. In conclusion, process steps that can be effective against viruses have a high potential for changing the nature of PEPs, thus having a potentially serious impact on the drug's quality, safety and efficacy. However, because there are almost no alternative resources on the market for lipases than PEPs, they still represent the only permitted drug compositions for the treatment of EPI.

In addition, for particular groups of patients, a disadvantage of the use of PEPs is the origin from pig. Usually, the pancreas of pigs is used, which cannot be tolerated by patients of Judaic or Islamic religion due to religious instructions. Furthermore pancreatin is a homogenate from the cells of pancreatic tissues (usually from pigs). Due to the rupture of a large number of acinic cells, it contains, in addition to pancreatic enzymes, a wide variety of other enzymes and proteins as well as further high and low molecular weight compounds. The composition of pancreatin is due to its industrial preparation process. To obtain pancreatin, pancreas of pigs are deep-frozen as quickly as possible after slaughtering, collected and broken up mechanically. For the stabilization and activation of the enzymes, various additives are added to the homogenate. This is followed by defatting with organic solvents, such as acetone, the removal of fibrous substances, and dewatering and drying by lyophilization. In view of the problems associated with the management of organic solvents and the costs thereof, there thus remains a need for a method of enzyme production which minimises the use of organic solvents or work without of organic solvents. For the preparation of particular dosage forms, further galenic processing may be effected into micropellets, tablets, capsules, pastes, creams, gels, oils or other formulations. Frequently, pancreatin based PEPs are mixed with various support materials and buffer substances. Further, granulated pancreatin is coated with acid-stable films or lacquers for protection against the low pH value of human gastric juice. The two latter processing steps are to ensure that the acid-labile PEPs can fulfill their digestive function at the target site, the duodenum (small intestine), but prevent the enzymes from being active in the acidic upper Duodenum of many pancreatitis Patients.

A newer PEP, which contains lipase, is Zenpep®. Zenpep® is a combination of porcine-derived lipases, proteases and amylases from pigs for slaughter indicated for the treatment of EPI due to cystic fibrosis or other conditions. In opposite to common marketed PEPs for EPI, Zenpep® does not show great variability in the amount of enzymes included in each capsule. The variability of the common PEPs is due in part to the manufacturer practice of overfilling capsules to account for enzyme degradation that occurs over the course of the product's shelf life. Variability in the product's enzyme content can lead to inconsistent therapeutic effects by either providing too much or too little of the required enzymes, which may lead to the suboptimal treatment of the patient's EPI. In addition, overfilled products may increase the risk of fibrosing colonopathy, which has been associated in some reports with long-term exposure to high-dose PERT. These problems can be avoided by the application of Zenpep®. However, Zenpep® contains the same porcine pancreatic lipase like common PEPs. In consequence porcine pancreatic lipase in Zenpep® becomes efficient only in the presence of porcine colipase in the duodenum. Thus, Zenpep® also nearly an unpurified protein mixture from pigs for slaughter, because purification in the manufacturing process would lead to a potential loss of the colipase. Additionally, Zenpep® can also contain viral contamination and, because of the necessary precipitation and defattening steps, residual organic solvents as described for PEPs. In consequence, as for common PEPs for PERT, porcine pancreatic lipase in this composition can be contaminated with viruses and/or organic solvents.

In order to circumvent the use of pig pancreatic tissue as source for lipase and protease, some researchers suggested the use of enzymes from fish or other marine animals generally described in FR No. 1015566, as well as compositions of enzymes from the gastrointestinal tract of krill (crustaceans from the class Euphausiaceae) and capelin fish (U.S. Pat. No. 4,695,457). However these natural resources are difficult to handle and to process for characterized enzyme preparations in industrial scale and in consequence enzyme preparation containing lipases from these origins never reached the market.

Due to the problems of contamination with viruses and organic solvents characterizing conventional enzyme preparation from pig pancreatic tissue, the use of microbially-derived enzymes as alternatives to porcine-derived PEP has been proposed. For example, U.S. Pat. No. 6,051,220 describes compositions comprising one or more acid stable lipases and one or more acid stable amylases, both preferably of fungal origin. United States patent application 2004/0057944 describes compositions comprising *Rhizopus delemar* lipase, *Aspergillus melleus* protease and *Aspergillus oryzae* amylase.

In part, some enzyme preparations therefore also contain microbial enzymes from mold extracts, such as Nortase® and Combizym®. In spite of their resistance to acid and although they do not depend on colipase, their clinical efficacy is low due to rapid intraluminal inactivation by bile salts and proteases.

A recombinant enzyme preparation in development, which contains a bile salt stable lipase, is a drug with the brand name Kiobrina, which is a recombinant human bile-salt-stimulated lipase (rhBSSL). This rhBSSL shall improve the digestion and absorption of essential fatty acids, such as long-chain poly-unsaturated fatty acids but also cholesterol esters in the human gut. rhBSSL is expressed and produced in mammalian cells and is developed by Sobi for enzyme therapy to improve growth and development in preterm infants receiving pasteurized breast milk and/or formula. The rationale for substitution of rhBSSL in pasteurized breast milk or infant formula is to restore the natural lipase activity level that is either lost on pasteurization or totally absent in formula. A disadvantage is, that the enzyme is active only in the presence of primary bile salts, which are often insoluble and, thus, not available in the duodenum, especially under the condition of exocrine pancreatic insufficiency. Furthermore the developing company Sobi announced that clinical data show that the rBSSL did not meet its primary endpoint and, thus, the rhBSSL is does not fulfill its function for enzyme substitution therapy in the human gastrointestinal tract.

Another recombinant lipase for the treatment of exocrine pancreatic insufficiency is the crystallized, purified cross-linked *Pseudomonas/Burkholderia cepacia* lipase with of molecular weight of 30 kDa, which is part of an enzyme composition named ALTU-135/TheraCLEC®/Trizytek®/Liprotamase®/Sollpura® (now with the brand name Sollpura®) developed by Anthera Pharmaceuticals and which is also disclosed in U.S. Pat. No. 7,718,169.

This microbial lipase is of bacterial origin, which is described in United States patent application 2001/0046493, can be produced by recombinant DNA technology. The enzyme is secreted in the culture medium, and requires a complex production process for purification and crystallization in order to stabilize the enzyme for administration in the human gastro intestinal system. After crystallization, the lipase crystals have to be chemically and covalently cross-linked in order reach sufficient acid stability. In vitro studies suggest that this modification called cross-linked enzyme crystals (CLEC) process increases stability of the lipase and that the cross-linked lipase is insoluble at acidic pH representative of the stomach. However, it has been shown that diffusion effects have been a serious problem for the practical use of crystalline enzymes (Alter, G. M., Leussing, D. L., Neurath, H. Bert L. Vallee, B. L., 1977) Kinetic Properties of carpoxipeptidase B in solution and crystals. Biochemistry 16 (16): 3663-3668). Furthermore it has been shown, that CLEC lipases show a significantly reduced enzyme activity on certain substrates compared to soluble enzymes (Margolin, A. L. (1995) Novel crystalline catalysts. Trends in Biotechnology 14 (7): 223-230).

Moreover, the *Pseudomonas/Burkholderia cepacia* lipase has a broad pH optimum from pH 4-8 with a strong decline of activity for pH values larger than 8. However, *Pseudomonas/Burkholderia cepacia* lipase is not active under pH conditions significantly larger than pH 8. In consequence this enzyme cannot support the digestion of lipids under strong alkaline conditions (larger than pH 8.5 or higher). One other problem for *Pseudomonas/Burkholderia cepacia* lipase is, that the enzyme is a protein from a pathogenic bacterium. *Pseudomonas/Burkholderia cepacia* (explanation: formerly known as *Pseudomonas cepacia*, the bacterium now is known as *Burkholderia cepacia*) is an important human pathogen which most often causes pneumonia in immunocompromised individuals with underlying lung disease such as cystic fibrosis or chronic granulomatous disease.

Patients with cystic fibrosis are at risk for acquiring the well known "Burkholderia cepacia syndrome and in consequence the so called "Burkholderia cepacia syndrome" is a serious condition in patients with cystic fibrosis that does not always respond well to treatment.

In the case of such a *Pseudomonas/Burkholderia cepacia* infection long-term active memory is acquired following infection by activation of B and T cells, while some of their offspring become long-lived memory cells. Throughout the lifetime of human, these memory cells as part of the "adaptive immune system", remember each specific pathogen encountered and can mount a strong response if the pathogen is detected again.

Under the conditions of oral treatment with *Pseudomonas/Burkholderia cepacia* lipase the oral uptake of enzymes from *Pseudomonas/Burkholderia cepacia* as part of enzyme replacement therapy (in the case of cystic fibrosis) represents an incorporation of exogenous antigens. The antigens will be detected by the adaptive immune system as pathogens and would result 1. in the activation of the immune system (so called immunological memory), 2. the generation of antibodies against the enzymes and 3. the risk of an exaggerated immune response in the intestine mucosa including potential allergic and autoimmune reactions and sepsis.

This risk of an of exaggerated immune response in the case of a medication of cystic fibrosis with *Pseudomonas/Burkholderia cepacia* enzymes would be counterproductive for the treatment of patients and would exacerbate the patients' health situation.

The combination of insufficient efficacy and the risk of the above described detrimental side effects have already raised serious concern of regulatory agencies. In 2011, the Gastrointestinal Drugs Advisory Committee of the Food and Drug Administration (FDA) of the US Department of Health and Human Services rejected the finding that Sollpura®'s (the enzyme preparation with *Pseudomonas/Burkholderia cepacia* lipase) benefits outweighed its risks, arguing that additional efficacy data were needed before it could conclude that it worked in patients better than existing porcine derived pancreatic enzyme products.

Finally it has been shown that there is substantial evidence that Sollpur® is less efficacious than the porcine-derived PEPs and appears to expose patients with EPI to greater risk (Carome M. Wolfe S. Testimony to the FDA Gastrointestinal Drug Advisory Committee regarding liprotamase—risk: benefit assessment; ethics of further clinical trials. Washington D.C.: Public Citizen Research Group. Jan. 12, 2011)

Moreover, the U.S. Pat. No. 5,998,189 discloses a recombinant acid stable dog gastric lipase produced in *E. coli* and claims the expression of acid stable dog gastric lipase in *E. coli* as well as in other prokaryotic and eukaryotic expression systems. Additionally, the expression and extraction of this acid stable dog gastric lipase in transgenic corn has been demonstrated Zhong, Q., GU, Gu, Z. and Glatz, C. E. (2006) Extraction of recombinant dog gastric lipase from transgenic corn seed. J. Agric. Food Chem. 54: 8086-8092).

However, dog gastric lipase shows a very low pH optimum at pH 4 with a very narrow pH profile from pH 3-pH 5 (Carriere, F., Moreau, H., Raphel, V., Laugier, R., Benicourt, C., Junien, J.-L. and Verger, R., 1991) Purification and biochemical characterization of dog gastric lipase. Eur. J. Biochem. 202: 75-83)

The goal of an enzyme preparation containing lipase displaying the highest efficacy at the lowest dose, and characterized by a well-defined safety profile, remains of great importance to all patients suffering from pancreatic insufficiency, including those in the cystic fibrosis community.

TABLE 1

Summary enzyme preparation for PERT approaches

| name and brand name on market | source | enzymes | pH otimum of lipase | remarks | limitations |
| --- | --- | --- | --- | --- | --- |
| PEPs (Creon ®, Cotazyme ®, Ultrase ®, Viokase ® etc.) | Pancreatin or pancreatic extract drug products from pig pancreas tissue | pancreatic enzymes from pig | 7 to 8 | | no biotechnological process, no containment process, so contamination with viruses and bacteria are possible due to non-steralized tissue from slaughter house |

TABLE 1-continued

Summary enzyme preparation for PERT approaches

| name and brand name on market | source | enzymes | pH otimum of lipase | remarks | limitations |
|---|---|---|---|---|---|
| Zenpep ® | Pancreatin or pancreatic extract drug products from pig pancreas tissue | pancreatic enzymes from pig with defined enzyme activity | 7 to 8 | | no biotechnological process, no containment process, so contamination with viruses and bacteria are possible due to non-sterilized tissue from slaughter house |
| no product | tissue from krill and capelin fish | lypolytic and proteolytic enzymes from gastrointestinal tract | no pH optimium disclosed | | no biotechnological process, no containment process, so contamination with viruses and bacteria are possible due to non-sterilized tissue with waste character of the natural source |
| Nortase ®/ Combizym ® | Microbial - mould fungus | *Rhizopus oryzae/delemar* lipase, *Aspergillus melleus* protease and *Aspergillus oryzae* amylase | 6.6 to 7.5 | | *Rhizopus oryzae/delmar* is an opportunistic human pathogen, potential immune reaction if previous *Pseudomonas/Burkholderia cepacia* infection, lipase unstable under physiological bile salt concentrations |
| Kiobrina ® | | recombinant human bile salt stable lipase (rhBSSL) | 7.3 to 8.6 | | complex and expensive recombinant production process in animal cell lines |
| ALTU-135/TheraCLEC ®/ Trizytek ®/ Lipratamase ®/ Sollpura ® | Microbial - culture of *E. coli* bacteria | recombinant *Pseudomonas/Burkholderia cepacia* lipase | 6.5 to 9 | cross-linked enzyme crystals (CLEC process) | *Pseudomonas/Burkholderia cepacia* opportunistic human pathogen, potential immune reaction if previous *Pseudomonas/Burkholderia cepacia* infection, low activity unter acidic conditions |
| no product | Microbial - culture of *E. coli* bacteria | acid stable dog gastric lipase produced in *E. coli* (http://www.google.com/patents/US5998189) | 3 to 5 | | low activity under alkaline conditions |
| Merispase ® | transgenic corn | acid stable dog gastric lipase in transgenic corn | 3 to 4 | | low activity under alkaline conditions |
| no product | Microbial - culture of *T. thermophila* | acid stable *Tetrahymena* lipases | 3.5 to 4.5 | | low activity under alkaline conditions |

In most patients, lipid digestion cannot be completely normalized by current standard therapy. Furthermore the production of lipases for human administration is cumbersome and expensive. The instant invention addresses these issues.

SUMMARY OF THE INVENTION

The present invention provides a medicament containing homologous expressed enzymes from ciliates for treating digestive disorders. The invention and general advantages of its features will be discussed in detail below.

DETAILED DESCRIPTION OF THE INVENTION

Figure 1:
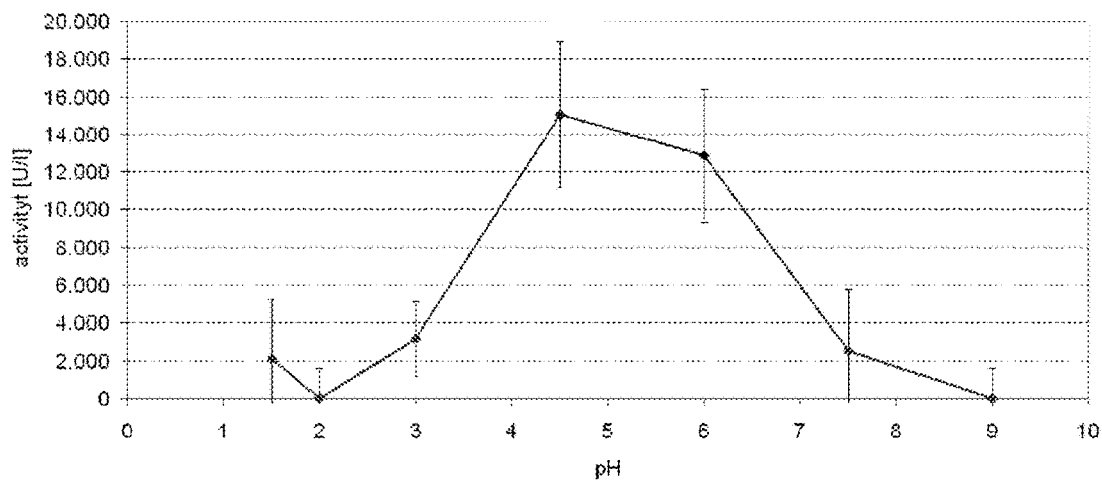
FIGS. 1-3 show the lipolytic activity of three different overexpressed *Tetrahymena* lipases at different pH values.

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a", "an", and "the" include singular and/or plural referents unless the context clearly dictates otherwise. It is moreover to be understood that, in case parameter ranges are given which are delimited by numeric values, the ranges are deemed to include these limitation values.

It is further to be understood that embodiments disclosed herein are not meant to be understood as individual embodiments which would not relate to one another. Features discussed with one embodiment are meant to be disclosed also in connection with other embodiments shown herein. If, in one case, a specific feature is not disclosed with one embodiment, but with another, the skilled person would understand that does not necessarily mean that said feature is not meant to be disclosed with said other embodiment. The skilled person would understand that it is the gist of this application to disclose said feature also for the other embodiment, but that just for purposes of clarity and to keep the specification in a manageable volume this has not been done.

Furthermore, the content of the prior art documents referred to herein is incorporated by reference. This refers, particularly, for prior art documents that disclose standard or routine methods. In that case, the incorporation by reference has mainly the purpose to provide sufficient enabling disclosure, and avoid lengthy repetitions.

According to one aspect of the invention, a combination of two or more lipase enzymes is provided, wherein at least one lipase enzyme has a pH optimum at an acidic pH value, while at least one other lipase enzyme has a pH optimum at an alkalic pH value.

One way to define the pH optimum is the pH range in which the lipase as >50% of its peak activity, as determined with, e.g., the Nixon Test or the titration test (see below). The term "pH optimum" is used synonymously with the term "maximum lipolytic activity".

The term "acidic pH value" means a pH between ≥0 and ≤7, while the term "alkalic pH value" means a pH between > and ≤14.

The term "lipase enzyme", as used herein, refers to an enzyme that catalyzes the hydrolysis of fats (lipids). Lipases are a subclass of the esterases and perform essential roles in the digestion, transport and processing of dietary lipids (e.g. triglycerides, fats, oils) in most, if not all, living organisms. The term lipases encompass the following subtypes: bile salt-dependent lipase, pancreatic lipase, lysosomal lipase, hepatic lipase, lipoprotein lipase, hormone-sensitive lipase, gastric lipase, endothelial lipase, pancreatic lipase related protein 2, pancreatic lipase related protein 1 and lingual lipase The inventors have surprisingly found that a combination of these two or more lipase enzymes wherein one of which has a pH optimum at an acidic pH value, while at least one other has a pH optimum at an alkalic pH value, significantly increases the efficacy of a lipase therapy.

According to one embodiment, the lipolytic activity of at least one lipase enzyme is determined with the Nixon Test or the titration test.

The Nixon test is disclosed in Nixon & Chang 1979, content of which is incorporated herein. Details of this test are disclosed elsewhere herein. The titration test is disclosed in United States Pharmacopeia 23, NF18 1095, pp 1150-1151, content of which is incorporated herein.

In one embodiment, the at least one lipase enzyme is a lipase enzyme encoded, expressed and/or produced by an organism of the order ciliates.

In one embodiment, said ciliate is from the family Tetrahymenidae. More preferably, said ciliate is from the genus *Tetrahymena*. Most preferably, said ciliate is from the *Tetrahymena thermophile*.

A ciliate based lipase production system provides an economical, simple and reliable method for the production of lipases, which have a drastically increased specific activity compared to the available competitors and thus a highly enhanced therapeutic potential.

Since no viruses have been found in *Tetrahymena* combined with the great evolutionary distance between mammalians and ciliates the safety of the product is expected to be much higher, while the production can be run with more stability and less risk of failure due to viral infections.

In one embodiment, at least one lipase enzyme is a lipase enzyme according to claim 3 which has been modified by site directed or random mutagenesis and subsequent selection.

In one embodiment, one lipase enzyme has a pH optimum at a pH value which occurs in the stomach of a mammal, while at least one other lipase enzyme has a pH optimum at a pH value which occurs in the lower small intestine of a mammal.

The intraluminal pH of a mammalian gastrointestinal tract including the stomach is discussed in Fallingborg J, Dan Med Bull. 1999 June; 46(3):183-96. Some typical values for human gastrointestinal tract are shown in the following table:

TABLE 2

| Stomach | pH 1-4 |
| Duodenum | pH 6 |
| terminal ileum | pH 7, 4 |
| caecum | pH 5, 7 |

Thus, due to it's broad pH spectrum, the product promotes lipolysis over the entire gastrointestinal tract.

In one embodiment, one lipase enzyme of the combination has a pH optimum at a pH value in the range of pH≥1 and ≤6.

In one embodiment, one lipase enzyme of the combination has a pH optimum at a pH value in the range of pH≥8 and ≤11.

In one embodiment, the at least two lipases comprise amino acid sequences selected from the group consisting of
  a) SEQ ID No 4-6, and/or fractions, variants, homologues, or derivatives of thereof
  b) amino acid sequences having a sequence identity of at least 70%, preferably 95% with any of SEQ ID No 4-6

These sequences relate to three preferred lipases shown in the following:

TABLE 3

| CILIAN No | pH optimum | amino acids | AA Sequence ID | DNA Sequence ID | Gene name | NCBI Gene ID: |
| --- | --- | --- | --- | --- | --- | --- |
| 10 | 3.5-7 | 288 | Seq ID No 4 | Seq ID No 1 | TTHERM_00320120 | 7825111 |
| 11 | 6-11 | 288 | Seq ID No 5 | Seq ID No 2 | TTHERM_00320130 | 7825112 |
| 14 | 2-5.5 | 308 | Seq ID No 6 | Seq ID No 3 | TTHERM_00320230 | 7825120 |

According to another embodiment of the present invention, a pharmaceutical preparation comprising the combination of two or more lipase enzymes according to the above description is provided.

According to still another embodiment of the present invention, the use of the combination of two or more lipase enzymes according the above description, or of a pharmaceutical preparation comprising the latter, for
- the treatment of a lipid digestion deficiency and/or a digestive disorder, or
- the manufacture of a medicament for the treatment of a lipid digestion deficiency and/or a digestive disorder.

is provided.

In one embodiment, in said use the digestive disorder is exocrine pancreatic insufficiency (EPI). Other digestive disorders that can be treated encompass steatorrhoea, celiac disease or indigestion EPI is the inability to properly digest food due to a lack of digestive enzymes made by the pancreas. EPI is found in humans afflicted with cystic fibrosis and Shwachman-Diamond Syndrome, and is caused by a progressive loss of the pancreatic cells that make digestive enzymes; loss of digestive enzymes leads to maldigestion and malabsorption of nutrients from normal digestive processes. Chronic pancreatitis is the most common cause of EPI in humans.

Steatorrhea is the presence of excess fat in feces. Stools may also float due to excess lipid, have an oily appearance and can be especially foul-smelling. An oily anal leakage or some level of fecal incontinence may occur. There is increased fat excretion, which can be measured by determining the fecal fat level. The definition of how much fecal fat constitutes steatorrhea has not been standardized.

Celiac disease is a condition in which gluten (a protein found in grains) damages the intestinal tract. Symptoms include abdominal pain, bloating, weight loss, and fatigue. People with celiac disease must follow a strict diet that includes no gluten. Lipases have been studied as part of the treatment for celiac disease, and therapy therewith results in a modest weight gain.

Indigestion is a condition in which patients suffer bloating, gas, and fullness following a high fat meal. These symptoms are commonly associated with irritable bowel syndrome (IBS), so some researchers speculate that pancreatic enzymes might help treat symptoms of IBS. No studies have been done, however.

In one embodiment, in said use the lipid digestion deficiency is Lipoprotein lipase deficiency, which is a condition caused by mutation in the gene which codes lipoprotein lipase.

According to still another embodiment of the present invention, the use of the combination of two or more lipase enzymes according the above description, or of a pharmaceutical preparation comprising the latter, for the treatment of Cystic fibrosis is provided.

Cystic fibrosis is an inherited condition that causes the body to produce abnormally thick, sticky mucus. Patients often have nutritional deficiencies because mucus blocks pancreatic enzymes from getting to the intestines. Taking lipases helps improve the nutrition these patients get from food.

According to yet another embodiment, a method of producing a combination of two or more lipase enzymes according to the above description is provided, which method comprises the steps of
- a) expressing the two or more lipase enzymes in one or more suitable production systems, and
- b) purifying the two or more lipase enzymes expressed in step a).

In one embodiment, in said method at least one lipase enzyme is produced by homologous expression in an organism of the order ciliates The term "homologous protein expression" relates to the expression of a gene or protein in an organism from where said gene or protein originates.

In one embodiment, said ciliate is from the family Tetrahymenidae. More preferably, said ciliate is from the genus *Tetrahymena*. Most preferably, said ciliate is from the *Tetrahymena* thermophile.

A ciliate based lipase production system provides an economical, simple and reliable method for the production of lipases, which have a drastically increased specific activity compared to the available competitors and thus a highly enhanced therapeutic potential.

Since no viruses have been found in *Tetrahymena* combined with the great evolutionary distance between mammalians and ciliates the safety of the product is expected to be much higher, while the production can be run with more stability and less risk of failure due to viral infections.

Further, a ciliate based lipase production system is particularly useful in case a ciliate lipase is to be produced, because ciliates have a codon usage that differs from other eukaryotes, as can be seen in the following table:

TABLE 4 fields: [triplet] [frequency: per thousand] ([number])

| | | | |
|---|---|---|---|
| UUU 26.1(3815) | UCU 24.4(3557) | UAU 23.3(3407) | UGU 9.7(1412) |
| UUC 19.4(2827) | UCC 6.5(948) | UAC 14.5(2110) | UGC 8.8(1282) |
| UUA 29.8(4346) | UCA 16.8(2453) | UAA 36.8(5366) | UGA 2.0(286) |
| UUG 14.1(2054) | UCG 1.5(222) | UAG 11.0(1606) | UGG 7.4(1080) |
| CUU 20.3(2955) | CCU 17.6(2574) | CAU 8.7(1267) | CGU 4.6(677) |
| CUC 10.3(1497) | CCC 4.6(676) | CAC 6.4(930) | CGC 0.9(136) |
| CUA 7.4(1078) | CCA 8.2(1202) | CAA 19.8(2894) | CGA 0.5(73) |
| CUG 2.6(378) | CCG 0.5(68) | CAG 3.3(477) | CGG 0.1( 8) |
| AUU 39.3(5733) | ACU 27.2(3968) | AAU 48.0(7002) | AGU 13.5(1963) |
| AUC 16.2(2367) | ACC 7.8(1140) | AAC 24.2(3530) | AGC 9.2(1344) |

TABLE 4-continued fields: [triplet] [frequency: per thousand] ([number])

| | | | |
|---|---|---|---|
| AUA 19.1(2783) | ACA 14.8(2153) | AAA 58.7(8562) | AGA 26.6(3887) |
| AUG 19.3(2811) | ACG 0.8(111) | AAG 34.3(5001) | AGG 2.8(412) |
| GUU 25.8(3763) | GCU 30.3(4428) | GAU 42.5(6208) | GGU 24.5(3576) |
| GUC 10.1(1469) | GCC 7.5(1098) | GAC 12.4(1815) | GGC 4.3(629) |
| GUA 11.6(1693) | GCA 11.8(1726) | GAA 58.2(8499) | GGA 15.1(2205) |
| GUG 3.1(451) | GCG 0.6(88) | GAG 11.2(1630) | GGG 1.5(216) |

Coding GC 32.53% 1st letter GC 38.64% 2nd letter GC 31.25% 3rd letter GC 27.69%

In one embodiment, in said method at least one lipase enzyme is produced by overexpression, preferably by homologous overexpression.

The term "homologous overexpression" relates to the over-expression of a gene or protein in an organism from where said gene or protein originates.

For this purpose, the expression of an endogenous gene can be enhanced by external factors, e.g., it is brought under the control of a promoter cloned in directly into the genome, or transcriptions factors are added to the respective cell or organism. As an alternative, the expression of a copy of said endogenous gene introduced into that cell or organism by means of a suitable plasmid can be provided. Examples for such plasmids are shown in FIGS. 6 and 7.

According to yet another embodiment of the invention, two or more nucleic acid molecules are provided, selected from the group consisting of
- a) at least one nucleic acid molecule comprising a nucleotide sequence presented as SEQ ID NO 1-3
- b) at least one nucleic acid molecule encoding a polypeptide comprising the amino acid sequence presented as SEQ ID NO 4-6
- c) at least one nucleic acid molecule that is a fraction, variant, homologue, or derivative of the nucleic acid molecules of a)-b),
- d) at least one nucleic acid molecule that is a complement to any of the nucleic acid molecules of a)-c), or capable of hybridizing therewith under stringent conditions,
- e) at least one nucleic acid molecule which comprises, in comparison to any of the nucleic acid molecules of a)-d) at least one silent single nucleotide substitution, nucleic acid molecule according to a) and c)-e) which is code optimized for a protozoan expression host, and/or
- f) at least one nucleic acid molecule having a sequence identity of at least 70%, preferably 95% with any of the nucleic acid molecules of a)-f).

Further Description

The inventors revealed 37 open reading frames for proteins with putative lipolytic activity in the genome of *Tetrahymena*. In the course of our experiments three enzymes were selected due to favorable properties by screening experiments.

*Tetrahymena* is a nonpathogenic unicellular eukaryotic microorganism which has been established in a few laboratories as an expression host. It features a number of advantages which make it suitable for homologous protein expression. *Tetrahymena* is a broadly examined model organism, and, in over 50 years of basic research, no viruses or endoparasites were observed. Examinations with indicator cell lines revealed no endogenous infectious agents like viruses or mycoplasm, which can infect higher animals. This might be due to the nuclear dimorphism which is common to ciliates. Another reason for this might be the unusual codon usage and AT-rich genome in Ciliates. The inventors do thus assume that pathogenic viruses of higher organisms cannot amplify in most ciliates. The fact that, as known so far, ciliates are not susceptible for viruses, arises as a surprising advantage. This means that in production processes based on Ciliates, amplification or growth of adventitious viruses does not occur. Furthermore it is possible to grow ciliates in animal free media. This means, that in case a protein is produced for therapeutic use, costly virus depletion procedures as necessary in industrial processes with human and animal cell cultures can be skipped.

First of all, the above considerations as related to codon usage in ciliates apply for *Tetrahymena* as well. Furthermore, high copy number plasmids are available for *Tetrahymena*, containing an origin of replication (ori) from a minichromosomal rDNA. This minichromosomal rDNA is present in up to 9.000 copies per cell. Beyond that stable integration can take place into the macronuclear DNA, in which all genes are present in 45-fold copy number. The high gene dose is the ideal precondition for an efficient protein biosynthesis and thus for a high productivity. In contrast to bacteria, ciliates of the genus *Tetrahymena* secrete biologically proteins very efficiently to the supernatant.

Batch, fed-batch and continuous fermentation of *Tetrahymena* with cell densities up to $2 \times 10^7$ cells/ml and dry weights of up to 80 g/L are established, and production enlargements (upscaling) up to 1000 L could be demonstrated without any problem. In feasibility studies with reporter proteins space-time yields of 50-90 pg/cell a day could already be achieved. First experiments with homologous expression resulted in a yield of over 200 mg/L a day for secreted proteins. *Tetrahymena* can be fermented in conventional production facilities for microbiological expression systems (bacteria or yeasts). This means that no costly modifications in existing production plants or a new building of the production facilities are necessary.

Ciliate systems have, however, some other advantages with respect to the expression of secreted enzymes. These will be discussed in the following.

Despite the said advantages, ciliate expression systems are still relatively unknown, and the person skilled in the art, when being asked about potential heterologous/homologous expression systems, would rather think of *E. coli*, yeast, insect cell systems (baculovirus) and mammalian cell lines.

Methods for the transformation of ciliates, which can be used in the context of the present invention, comprise, among others, microinjection, electroporation and particle bombardment, and are, for example, described in Tondravi & Yao (1986), Gaertig & Gorovsky (1992) and Cassidy-Hanley et al (1997).

Methods for transformation and heterologous protein expression have been described for a few protists (WO 00/58483 and WO 00/46381). The generation of mitotically stable transformants of the ciliate *Tetrahymena thermophila* can be achieved after transfection either of the somatic macronucleus or the generative micronucleus by microinjection, electroporation or by particle bombardment.

Selection of the transformants can be performed using different selection markers like the neomycin resistance (Weide et al. 2006, BMC) and the integration of the heterologous genes by homologous DNA recombinantion, which results in stable thymidin-auxotrophic *Tetrahymena* cells (Weide et al. 2006, BMC). In addition, the use of blasticidin S (Weide et al. 2006, BMC) or paclitaxcel (WO 00/46381) resistance has also been considered.

Promoters suitable for lipase expression in ciliates are, for example, disclosed in WO2007006812A1 which is also registered for the applicant of the present invention, the content of which shall be incorporated herewith by reference. Therein, a heat-inducible promoter and a metallothionein-promoter are disclosed which can also be used for the purposes of the present invention.

Furthermore, a vector for the transfection of a ciliate host cell is provided, said vector comprising at least one nucleic acid molecule encoding for a lipase.

Surprisingly a combination of *Tetrahymena* lipases and proteases, hereinafter referred to as "the preparation", can meet the requirements for the treatment of pancreatic malfunction better than any product on the market or currently under development. Firstly, the unparalleled ability of lipid digestion under various pH conditions ranging from pH values of 2 to pH values of up to 11 enables the preparation to digest lipids in the acidic gut and the, due to pancreatic dysfunction, acidic upper duodenum as well as in the more neutral to basic parts of the small intestine. Secondly, the preparation's specific activity surprisingly was found to be at least one order of magnitude higher than the specific activity of pancreatin even under neutral to basic conditions. This will help to promote the patient's compliance by reducing his daily pill burden. Thirdly a predefined mixture of enzymes is contraindicated for certain forms of pathological maldigestion.

In a preferred embodiment of the present invention, two or more *Tetrahymena* lipases cover the physiological pH range of the gastrointestinal tract enabling lipolysis from the stomach to the lower small intestine. In another preferred embodiment an alkaline *Tetrahymena* lipase is used to digest lipids in the alkaline environment of the duodenum.

The possibility of a modular assembly of lipase, protease and amylase activity allows the adaptation of the preparation to patients with different conditions and thus different needs of medications. For example high amylase content is undesirable for children with mucoviscidose.

Proteases are contraindicated in patients with acute pancreatitis or active episodes of chronic pancreatitis. And fourthly, the preparation, in contrast to lipases from funghi is activated by bile acids in physiologic concentrations.

Definitions

The term "ciliate", as used herein, shall refer to the scientific phylum of Ciliophora, which are unicellular eukaryotes ("protozoa" or "protists") characterized, among others, by their relatively large size (some species have up to 2 mm in length), their ciliated cell surface and by two different sorts of nuclei, i.e., a small, diploid micronucleus, and a large, polyploid macronucleus (used for protein expression). The latter is generated from the micronucleus by amplification of the genome and heavy editing.

The term "cDNA", as used herein, shall refer to a DNA molecule which encodes for a protein to be expressed, and is devoid of any non-encoding parts, like introns. In many cases, a cDNA has been directly synthesized from an mRNA template using reverse transcriptase, and an oligo dT-primer. However, the term shall as well comprise synthetic genes and encoding DNAs otherwise obtained.

The term "promoter", as used herein, shall refer to a regulatory region of DNA generally located upstream (towards the 5' region of the sense strand) of a gene or a cDNA, that allows or even enhances transcription of the gene, or the cDNA.

The term "fragment", as used herein, shall refer to a part of a protein which lacks some parts, or domains, of the native, or wildtype protein while retaining some activity in terms of enzymatic activity, immunogenity, target binding or the like.

The term "signal sequence", as used herein, shall refer to a nucleic acid sequence which encodes for an oligopeptide ("signal peptide") which directs proteins synthesized in the cytosol to certain organelles such as the nucleus, mitochondrial matrix, endoplasmic reticulum, chloroplast, apoplast and peroxisome. Some signal peptides are cleaved from the protein by signal peptidase after the proteins are transported. In a stricter sense, the signal sequence, or the signal peptide, accounts for the secretion of the said protein into the exterior medium. This process takes place via the rough endoplasmic reticulum, the Golgi apparatus and subsequent exocytosis. In many cases a signal sequence is located at the N-terminus of the protein to be secreted.

The term "operably linked" as used herein, means that a nucleotide sequence, which can encode a gene product, is linked to a promoter such that the promoter regulates expression of the gene product under appropriate conditions. Two nucleotide sequences that are operably linked contain elements essential for transcription, including, for example, a TATA box.

The term "nucleic acid molecule" is intended to indicate any single- or double stranded nucleic acid molecule comprising DNA (cDNA and/or genomic DNA), RNA (preferably mRNA), PNA, LNA and/or Morpholino.

The term "stringent conditions" relates to conditions under which a probe will preferably hybridize to its target subsequence and much less to other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion (or other salts) at pH 7.0 to 8.3 and the temperature is at least about 30° C. for short probes (e.g. 10 to 50 nucleotides) and at least about 60° C. for longer probes. Stringent conditions may also be achieved with the addition of destabilizing agents, such as formamide and the like.

The term "fragment of the nucleic acid molecule" is intended to indicate a nucleic acid comprising a subset of a nucleic acid molecule according to one of the claimed sequences. The same is applicable to the term "fraction of the nucleic acid molecule".

The term "variant of the nucleic acid molecule" refers herein to a nucleic acid molecule which is substantially similar in structure and biological activity to a nucleic acid molecule according to one of the claimed sequences.

The term "homologue of the nucleic acid molecule" refers to a nucleic acid molecule the sequence of which has one or more nucleotides added, deleted, substituted or otherwise chemically modified in comparison to a nucleic acid molecule according to one of the claimed sequences, provided always that the homologue retains substantially the same binding properties as the latter.

The term "sequence identity of at least X %", as used herein, refers to a sequence identity as determined after a sequence alignment carried out with the family of BLAST algorithms (particularly megablast, discontiguous megablast, blastn, blastp, PSI-BLAST, PHI-BLAST, blastx, tblastn and tblastx), as accessible on the respective internet domain provided by NCBI.

The term "vector", as used herein, refers to a molecular vehicle used to transfer foreign genetic material into another cell. The vector itself is generally a DNA sequence that consists of an insert (gene of interest) and a larger sequence that serves as the "backbone" of the vector. The purpose of a vector to transfer genetic information to another cell is typically to isolate, multiply, or express the insert in the target cell. Vectors called expression vectors (expression constructs) specifically are for the expression of the transgene in the target cell, and generally have a promoter sequence that drives expression of the transgene. Simpler vectors called transcription vectors are only capable of being transcribed but not translated: they can be replicated in a target cell but not expressed, unlike expression vectors. Transcription vectors are used to amplify their insert.

The term "plasmid", as used herein, refers to Plasmid Vectors, i.e. circular DNA sequences that are capable of automatically replicating in a host cell. Plasmid vectors comprise an origin of replication ("ORI") that allows for semi-independent replication of the plasmid in the host cell. Furthermore, a plasmid may comprise a multiple cloning site which includes nucleotide overhangs for insertion of an insert, and multiple restriction enzyme consensus sites to either side of the insert, a promoter to drive transcription of the plasmid's transgene, optionally at least one genetic marker for confirmation that the plasmid has integrated with the host genomic DNA, and, optionally, a reporter for identification of which cells have been successfully transfected.

The term "host cell", as used herein, has two different meanings which may be understood according to the respective context. In the context of homologous protein expression, the term "host cell" refers to a cell which is used as expression host. Said cell, or its progenitor, has thus been transfected with a suitable vector comprising the cDNA of the protein to be expressed.

As used herein, the term "ciliate host cell" shall refer to a cell from the phylum Ciliophora (formerly: *Ciliata*), e.g., protozoans characterized by the presence of hair-like organelles called cilia and a nuclear dimorphism.

As used herein, the term "incorporated" shall refer to the fact that the said nucleic acid has entered the host cell in such way that it is ready for protein expression. Such incorporation can have different types in ciliates, e.g. "episomal incorporation" (e.g. the nucleic acid molecule, like a plasmid, has not entered the cellular nucleus, but replicates, and is translated, in the cytoplasm), and "integrative incorporation" (e.g. the nucleic acid molecule has integrated into the cellular genome).

Disclaimer

To provide a comprehensive disclosure without unduly lengthening the specification, the applicant hereby incorporates by reference each of the patents and patent applications referenced above.

The particular combinations of elements and features in the above detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. Furthermore, reference signs used in the description and claims do not limit the scope of the invention as claimed.

BRIEF DESCRIPTION OF THE EXAMPLES AND DRAWINGS

Additional details, features, characteristics and advantages of the object of the invention are disclosed in the subclaims, and the following description of the respective figures and examples, which, in an exemplary fashion, show preferred embodiments of the present invention. However, these drawings should by no means be understood as to limit the scope of the invention.

EXAMPLES AND FIGURES

1. Construction of Expression Vectors

Figure 6A:
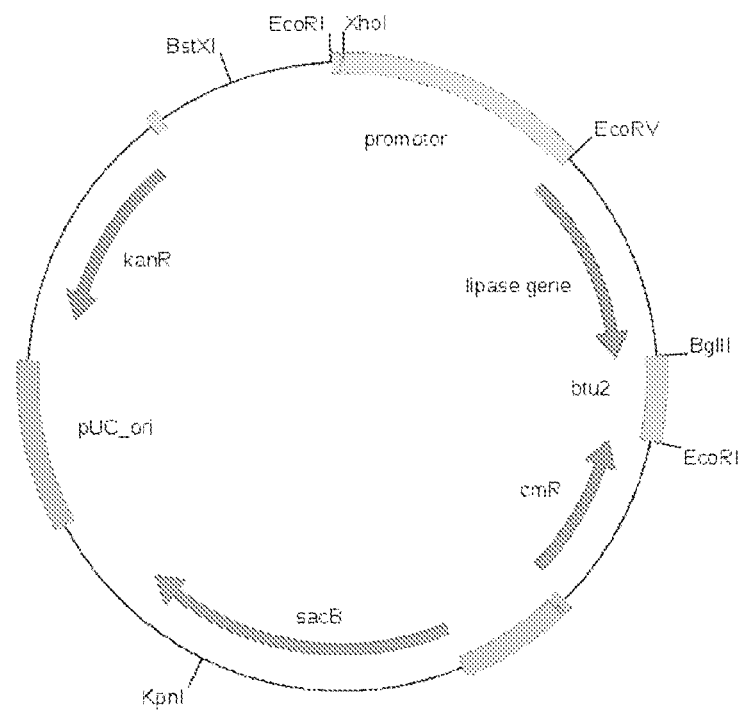
FIG. 6A shows a donor vector and FIG. 6B shows an acceptor vector used in the context of the present invention.
Figure 6B:
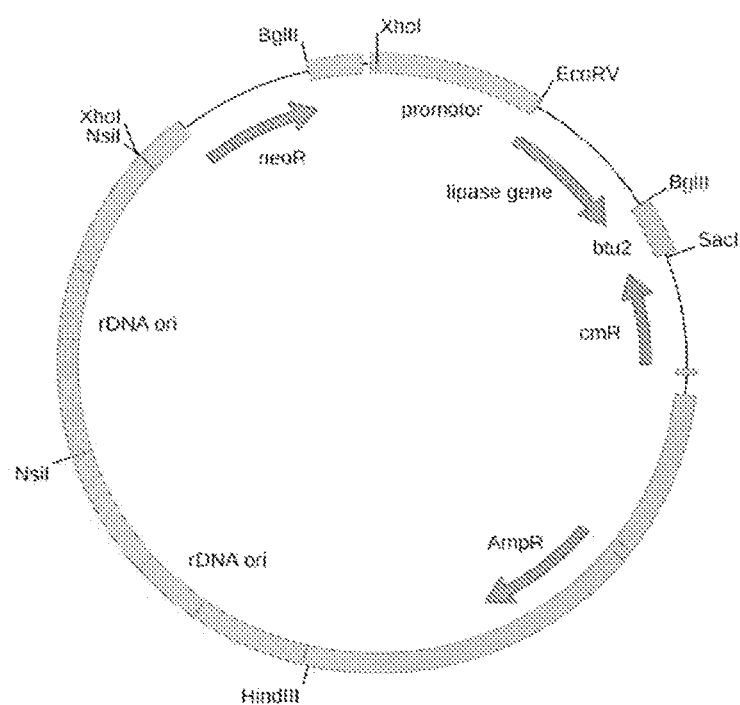
Figure 7A:
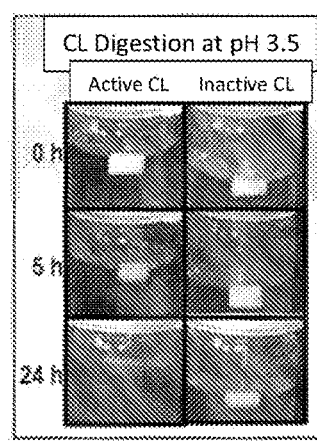
FIGS. 7A, 7B, and 7C show CL activity. A) Lipolysis of pig fat. Activated and heat inactivated CL was incubated with fat at 37° C. B) Specific activity of CL and standard enzyme at different pH values. The lipolytic activity was determined by pH-STAT and pH-endpoint titrations in an olive oil-water-emulsion in the presence of bile salt (Na-taurocholat) at 37° C. C) Activity of CL and standard enzyme at different temperatures. The lipolytic activity was determined by pH-STAT and pH-endpoint titrations in an olive oil-water-emulsion in the presence of bile salt (Na-taurocholat) at temperatures between 5-60° C.
Figure 7B:
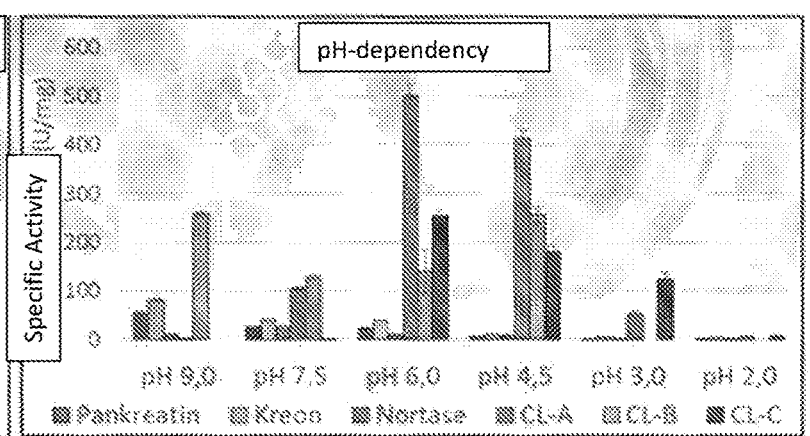
Figure 7C:
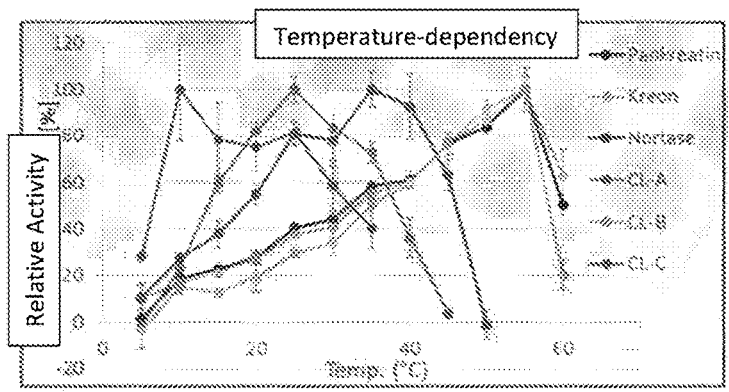

The genes for the different Lipases (SEQ ID No: 1, SEQ ID No: 2 and SEQ ID No: 3)) were cloned into the donor vector (see FIG. 6A). The expression cassettes from all donor vectors were transferred into the acceptor vector (see FIG. 6B) using a Cre dependent recombinase system. Sequences are given below.

2. Cultivation of Wildtype *Tetrahymena* and Transformation of Expression Plasmids (Biolistic Bombardment)

*Tetrahymena thermophila* strains B 1868/4, B 1868/7 and SB 1969 were cultivated in SPPR (2.5% proteose peptone, 1% Peptone acid hydrolysate, 0.5% yeast extract, 0.1% ferrous sulphate chelate solution and 0.2% glucose). We used conjugating *T. thermophila* strains. The transformation of the *T. thermophila* cells was performed as previously described in Cassidy-Hanley et al. 1997.

3. Determination of Lipase Activity

Transformed *Tetrahymena* clones were cultivated in SPPR medium by the addition of 400 µg/ml paromomycin at 30° C. in a 500 ml Multifermenter. Target gene expression was induced by addition of 0.55 µM $Cd^{2+}$ (MTT1) at the beginning of the cultivation or in early or mid log phase.

Aliquots of cell free SPPR supernatants were harvested about 20 h to 25 h after induction of the culture. Lipase activity of supernatants was determined by the colorimetric determination of liberated fatty acids described by Nixon & Chang (1979), or by titration (United States Pharmacopeia 23, NF18 1095, pp 1150-1151). The screening for lipolytic active clones was done by a Rhodamine fluorescence test (Jette & Ziomek, 1994).

Figure 2:
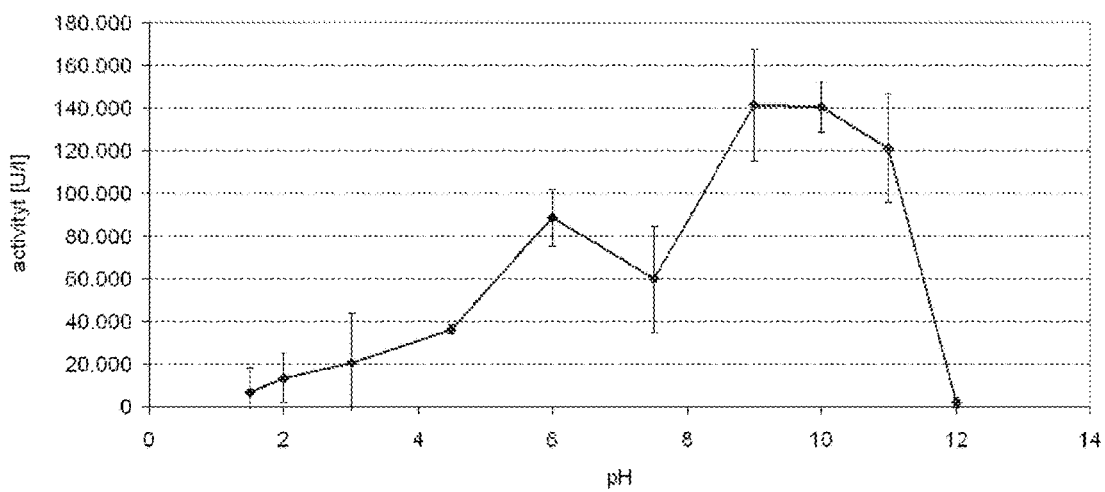
Figure 3:
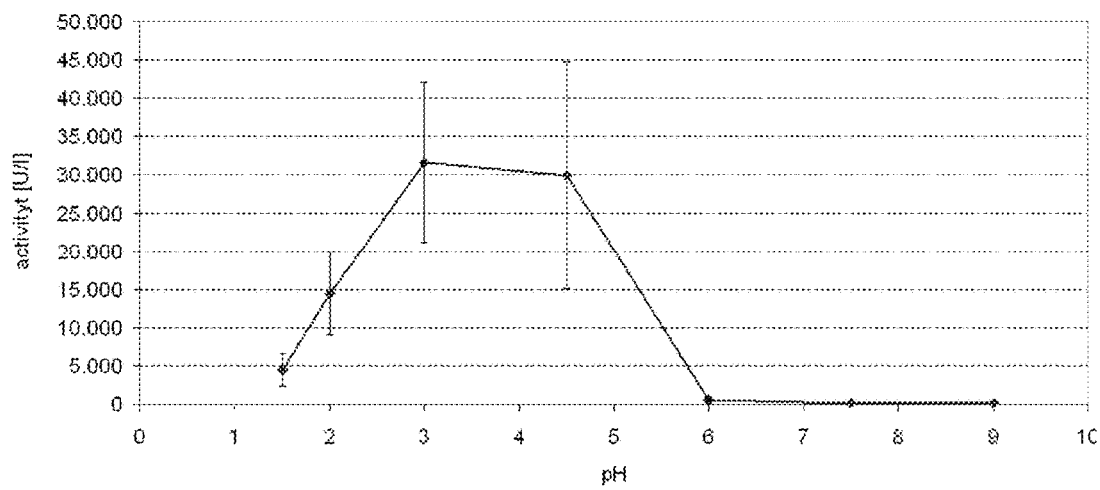

4. pH Spectra of Different *Tetrahymena* Lipases (FIGS. 1-3)

The lipolytic activity of three different overexpressed *Tetrahymena* lipases was tested at different pH values with the Nixon test. As substrate a high fat pig diet from Arie Blok (Woerden, N L) which was predigested with Pepsin at low pH to simulate gastric passage was used. Lipases No. 10 and 14 (SEQ ID NOs 4, and 6, respectively) showed activities at low pH values while lipase no. 11 exhibited a broad pH activity spectrum from neutral to high pH values comparable to Pancreatin. A combination of these lipases can cover pH values from 2 to 11. Results are shown in FIGS. 1-3.

Figure 4:
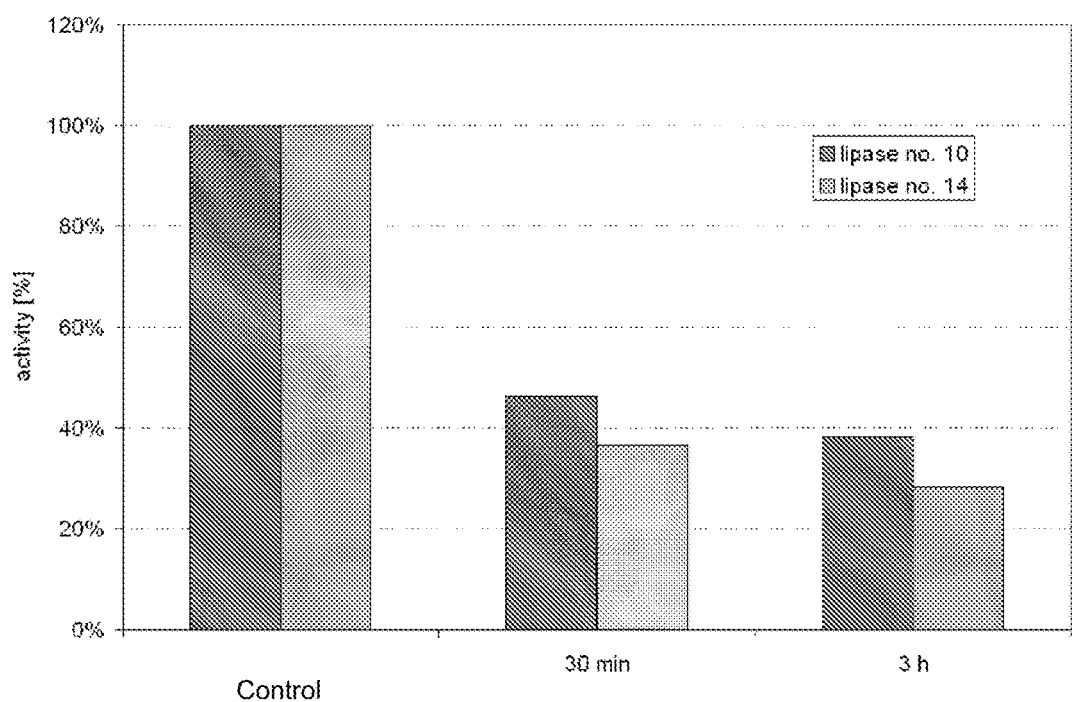
FIG. 4 shows the stability of two lipases in human gastric fluid.

5. Stability in Gastric Juice (FIG. 4)

pH activities were determined after incubation for 0.5 and 3 h in human gastric fluid (FIG. 4). In contrast to Pancreatin derived products lipases No. 10 and 14 retain activities of 38% and 30% respectively even after 3 h of incubation in human gastric fluid. Results are shown in FIG. 4.

Figure 5:
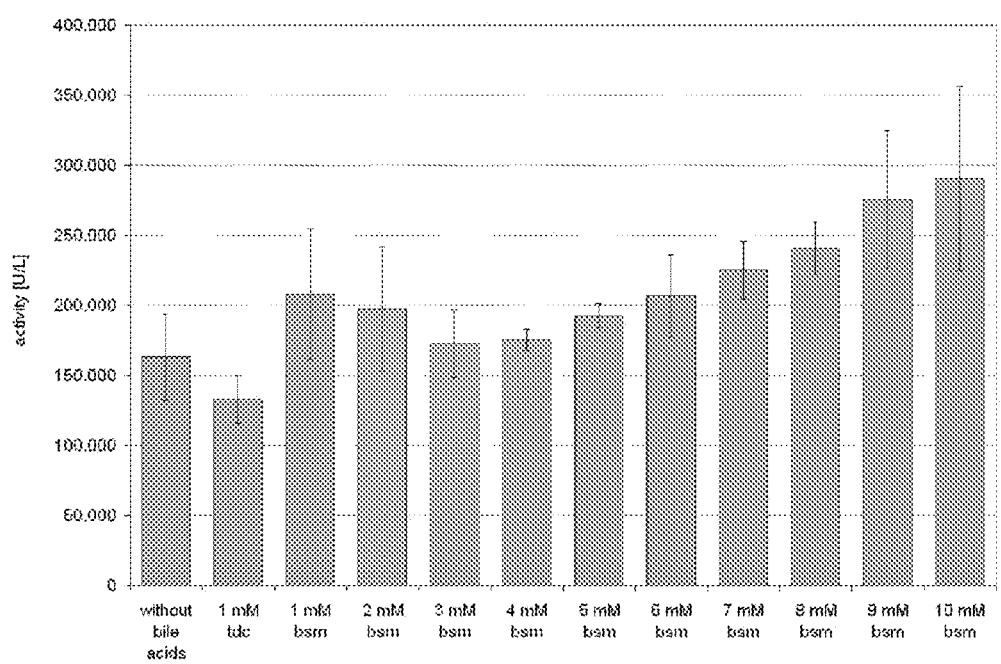
FIG. 5 shows the lipolytic activity of a lipase in the presence of various amounts of a physiologic mixture of bile acids.

6. Bile Salt Activation (FIG. 5)

The lipolytic activity of lipase No. 11 (SEQ ID No 5) was tested in the presence of various amounts of a physiologic mixture of bile acids (Gargouri et al., 1986). Like human pancreas lipase, lipase No. 11 is activated by increasing concentrations of bile acids. Results are shown in FIG. 5.

Sequences

```
SEQ ID No 1: Nucleotide of Lipase 10
  1     atgaaattgt aattgcttct attggtttgc ttgtcatttg ctgcctgcta atcatttact 61     tatacttaat cacttgctta agacttagct ggtttctctc ttgcttctta ctgtaatcct 121     aaatctatag aacaatggaa ttgtggatgt gcttgtgata aaaaccctta aggacttcga 181     aatgttacta tcttatttaa ctctactcta taagctagtg gatatttagg ctactccact 241     catcatgatg caattgttgt tgtattcaga ggaacagtac cttggttaat cgaaaattgg 301     attgctgact taaacacctt caagacttag tacccactct gccaaaactg ttatgtccat 361     taaggctttt ataaccagtt caaataattg aaatctcagc ttgttactag ctttacttca 421     cttcgttaac tatatcctaa tgcaaaagta tttgttacag gacattctct tggtgctgca 481     atgagtgctc actcaatacc agtaatttac taattaaatg gaaataaacc tattgatgct 541     ttttacaatt atggttgtcc tagagtaggt gactaaactt atgcaaactg gtttaacagt 601     taaaattttg ccttagaata tggtagaatt aataatgctg ctgatccagt tcctcattta 661     cctcctcttc tttacccatt ttcattttc cactacaacc atgaaatatt ctatccttct 721     tttgttcttt ttggaaacta acataactaa tgttaaaacg cggaaacaat atttggtgca 781     gatggagtaa taatagcagc taatgttcta gaccatctaa cttattttgg atgggattgg 841     tctggttcta tattaacttg ctaatga SEQ ID No: 4: amino acid sequence of Lipase 10
MKLQLLLLVCLSFAACQSFTYTQSLAQDLAGFSLASYCNPKSIE

QWNCGCACDKNPQGLRNVTILFNSTLQASGYLGYSTHHDAIVVVFRGTVPWLIENWIA

DLNTFKTQYPLCQNCYVHQGFYNQFKQLKSQLVTSFTSLRQLYPNAKVFVTGHSLGAA

MSAHSIPVIYQLNGNKPIDAFYNYGCPRVGDQTYANWFNSQNFALEYGRINNAADPVP

HLPPLLYPFSFFHYNHEIFYPSFVLFGNQHNQCQNAETIFGADGVIIAANVLDHLTYF

GWDWSGSILTCQ
SEQ ID No: 2: Nucleotide of lipase 11
  1     atgaaatcaa tttttttatt aattatttcc ttgcttttag cttcttgctc atagttttaa 61     tataatgaaa cacttgccta agacttagct ggattttctc ttgcttctta ctgtaatcct 121     aaatatttat aataatggaa ttgtggctct gcttgtaaaa aaaacccaaa tggtcttaca 181     gatttctctt atttgtataa caagactta aaggcaagtg gatatatagg ctattctgct 241     catcatgatg ctattatagt tgtctttaga ggaactgtcc cttggttgat ctaaaattgg 301     attgcagatt taaacactat caaaatttaa tatcctttct gtgaaaattg ttatgttcat 361     aaaggtttct ataaatagtt caattaatta aaatcttaac ttatttaaag cttacagaa 421     attcgttaaa aatatccttc atcaaaaata tttgtcactg gacattctct tggtgcagct 481     atgagttttc attcaatgcc tattattttt gaattaaatg gaaataagcc tattgatgct
```

```
541   ttctataatt atggttcccc aagagttggt aacgaagcat atgcaacttg gtttaattta
601   caaaattttg ctttataata tggcagaata aataatgcag cagatcctgt tcctcattta
661   cctcctattc ctttataatt ctaattttat catactaatc atgaaatatt ttatacttca
721   tttattgaag atggtaacaa atatgagtaa tgcttagatg cagaacacaa attatgtgca
781   aatagtaaga ttattgctgc aagcgttcgt gaccatctta gttattttgg ctggaattgg
841   gctacttcta ttttaacttg ccaatgaatt aaaaaattaa tttatcaaac aaaaacatta
901   actaaaatta tttttatctg tttaaatttg ttttaaaaca tttatatttt attttaatat
961   ttactacttt ttagaataaa atatct
```

SEQ ID No: 5: Amino acid sequence of lipase 11
MKSIFLLIISLLLASCSQFQYNETLAQDLAGFSLASYCNPKYLQ

QWNCGSACKKNPNGLTDFSYLYNKTLKASGYIGYSAHHDAIIVVFRGTVPWLIQNWIA

DLNTIKIQYPFCENCYVHKGFYKQFNQLKSQLIQSFTEIRQKYPSSKIFVTGHSLGAA

MSFHSMPIIFELNGNKPIDAFYNYGSPRVGNEAYATWFNLQNFALQYGRINNAADPVP

HLPPILFPFQFYHTNHEIFYTSFIEDGNKYEQCLDAEHKLCANSKIIAASVRDHLSYF

GWNWATSILTCQ

SEQ ID No: 3: Nucleotide acid sequence of lipase 14
```
   1  ATGAACAAAT TGCAAGTTCT TTTCATTGCA GCTATAGTTT GCACAATTGG ATCCACTGTT
  61  TATTTACTCA ATAAGAGCTC TTCAGATGTC CAAGAGTCTT AACTGACTTT CCCCTATGAT
 121  GAAAATTTAG CTGAAAATTT AGCTGGATTT TCTATGGCTT CTTATTGTAA AGCTTCTAAA
 181  ATTGAAAACT GGAATTGCGG TGCTTCTTGC AAAAAAAATC CCGAAGGACT TAAGATGTC
 241  TACATTATGA AAAATAAAAC TATGAACGCT GCTGGTTTCT TAGCATATTC TCCTGCTCAT
 301  GATGCTATAG TAGTTGTATT TAGAGGAACT GTCCCCTGGT TGATCAAGAA TTGGATTAGT
 361  GACATTAACA CTGTCAAAAC AAAATACTCT AGATGCGAAA ATGCTATGT TCATTTGGGC
 421  TTCTTCAATG CCTTCAAGGA ATTGTAAGAT TAAATTCTTA CTGAGTTCCC TAAACTTAAG
 481  GCCAAATATC CTTATTCAAA GGTAATTTAA CACAAAATAT ACATATATCT CTTTATAAAT
 541  AATTCATGCT ATCATATGTT TTTCTTTAGA TTATTGTGTA TTTCAAAAGC ATCACCTTAG
 601  CCTTTAAATA TTGATTAAGG AAATATTAAA TGATTTGTAA ATCAATTGC AAGAATATAA
 661  ATTACTCTAA ATTAAATCGA CGTATGAATC GAATACCCAA CTAATTATAG GCATTAATAA
 721  ATTTTGGAAA ATTATTTGTT TTCTCAATTT TCAATATGAA ATTTAGCTT AACTTATTTG
 781  GCTTTTAATA TTTATTCCAC TTTTTACATC TTATTCATCA ATTATATTTA TTTTAAACTC
 841  ATTTAAAAAT AAATAGGTTT TTGTTACAGG TCATTCCCTT GGTGCTGCAA TGAGTACTCA
 901  CGCTGTTCCT GTCATTTATG AACTCAATGG AAATAAGCCT ATCGATGCAT TCTATAATTT
 961  TGGTTCCCCT AGGGTTGGTG ATGAAAATTA CCACTAATGG TTCGATAGCT AAAATTTTAC
1021  TCTTTAATAT GGTAGAATTA ACCACAGAGC TGATCCAGTT CCTCATTTAC CCCCTAATTA
1081  CTCTCCTTTC ACTTTTACTC ATATTGATCA TGAAGTTTTC TATTAAACAT TTAAGAAACC
1141  TTATACATAA TGTATTGAAA CTGAAAGTCT TGAATGTGCT GATGGTATAAAAATTCCCTT
1201  AGATATTCCT GACCATCTTT CTTACTTTGG TTGGGATTGG GCCACTGACA TCTTAGCTTG
1261  CTAATGA
```

SEQ ID No: 6: amino acid sequence of lipase 14
MNKLQVLFIAAIVCTIGSTVYLLNKSSSDVQESQLTFPYDENLAE

NLAGFSMASYCKASKIENWNCGASCKKNPEGLQDVYIMKNKTMNAAGFLAYSPAHDAIV

VVFRGTVPWLIKNWISDINTVKIKYSRCEKCYVHLGFFNAFKELQDQILTEFPKLKAKY

-continued

PYSKVFVTGHSLGAAMSTHAVPVIYELNGNKP1DAFYNFGSPRVGDENYHQWFDSQNFT

LQYGRINHRADPVPHLPPNYSPFTFTHIDHEVFYQTFKKPYTQCIETESLECADGIKIP

LDIPDHLSYFGWDWATDILACQ

REFERENCES

Alter G M, Leussing D L, Neurath H, Vallee B L (1977): Kinetic properties of carboxypeptidase B in solutions and crystals. Biochemistry. August 9; 16(16):3663-8.

Tondravi, M M; Yao, M-C (1986): Transformation of *Tetrahymena thermophila* by microinjection of ribosomal RNA genes. PNAS 83, 4369-4373.

Gaertig, J; Gorovsky, M A (1992): Efficient mass transformation of *Tetrahymena thermophila* by electroporation of conjugants. PNAS 89, 9196-9200.

Cassidy-Hanley, D.; Bowen, J.; Lee, J.; Cole, E.; VerPlank, L.; Gaertig, J.; Gorovsky, M. & Bruns, P. Germline and somatic transformation of mating *Tetrahymena thermophila* by particle bombardment. Genetics, 1997, 146, 135-47.

Nixon M, Chan S H. A simple and sensitive colorimetric method for the determination of long-chain free fatty acids in subcellular organelles. Anal Biochem. 1979 Sep. 1; 97(2): 403-409

Weide, T.; Herrmann, L.; Bockau, U.; Niebur, N.; Aldag, I.; Laroy, W.; Contreras, R.; Tiedtke, A. & Hartmann, M. W. W.: Secretion of functional human enzymes by *Tetrahymena thermophila*. BMC Biotechnol, Vol. 6, pp. 19, 2006

Gargouri, Y.; Pieroni, G.; Lowe, P.; Sarda, L. & Verger, R.: Human gastric lipase. The effect of amphiphiles. In: Eur J Biochem 156 (1986), Nr. 2, S. 305-10

Jette J. F. & Ziomek E. (1994): Determination of lipase activity by a rhodamine-triglyceride-agarose assay. Anal. Biochem 219, 256-260

Margolin, A. L. (1995) Novel crystalline catalysts. Trends in Biotechnology 14 (7): 223-230)

Carome M. Wolfe S. Testimony to the FDA Gastrointestinal Drug Advisory Committee regarding liprotamase—risk: benefit assessment; ethics of further clinical trials. Washington D.C.: Public Citizen Research Group. Jan. 12, 2011)

Zhong, Q., G U, Gu, Z. and Glatz, C. E. (2006) Extraction of recombinant dog gastric lipase from transgenic corn seed. J. Agric. Food Chem. 54: 8086-8092).

Carriere, F., Moreau, H., Raphel, V., Laugier, R., Benicourt, C., Junien, J.-L. and Verger, R., 1991) Purification and biochemical characterization of dog gastric lipase. Eur. J. Biochem. 202: 75-83

United States Pharmacopeia 23, NF18 1095, pp 1150-1151

Fallingborg J, Dan Med Bull. 1999 June; 46(3):183-96.

Giuliano C A1, Dehoorne-Smith M L, Kale-Pradhan P B (2011) Pancreatic enzyme products: digesting the changes. Ann Pharmacother. 45(5):658-66.

What is claimed is:

1. A method of treating a lipid digestion deficiency in a subject, the method comprising administering a combination of two or more lipase enzymes to the subject, wherein at least one of the two or more lipase enzymes has a pH optimum at a pH value in the range of ≥1 and ≤6 and wherein the second lipase enzyme has a pH optimum at a pH value in the range of ≥8 and ≤11.

2. The method of claim 1, wherein the lipid digestion deficiency is exocrine pancreatic insufficiency.

3. The method of claim 1, wherein the at least one of the two or more lipase enzymes has lipolytic activity that is determined by a Nixon Test or a titration test.

4. The method of claim 1, wherein the at least one of the two or more lipase enzymes is a lipase enzyme encoded, expressed and/or produced by an organism of order of ciliates.

5. The method of claim 4, wherein the lipase enzyme has been modified by site directed or random mutagenesis and subsequent selection.

6. The method of claim 1, wherein at least one of the two or more lipase enzymes has a pH optimum at an acidic pH value which occurs in the stomach of a mammal and wherein the second lipase enzyme has a pH optimum at an alkali alkaline pH which occurs in the lower small intestine of a mammal.

7. The method of claim 1, wherein the two or more lipase enzymes comprise an amino acid sequence selected from the group consisting of SEQ ID NOs: 4, 5, or 6, fractions, variants, homologues or derivatives thereof; an amino acid sequence having a sequence identity of at least 70% with SEQ ID NOs: 4, 5 or 6; or an amino acid sequence having a sequence identity of at least 95% with SEQ ID NOs: 4, 5 or 6.

\* \* \* \* \*

UNITED STATES PATENT AND TRADEMARK OFFICE
CERTIFICATE OF CORRECTION

PATENT NO.        : 10,590,402 B2
APPLICATION NO.   : 15/545583
DATED             : March 17, 2020
INVENTOR(S)       : Marcus Wolf William Hartmann and Ingo Aldag It is certified that error appears in the above-identified patent and that said Letters Patent is hereby corrected as shown below:

In the Specification

In Column 8, Table 1, the pH of the seventh row should read -- 8.5 to 9 -- instead of -- 6.5 to 9 --

In Column 10, Table 2, Line 36, the pH value should read -- 7.4 -- instead of -- 7, 4 --

In Column 10, Table 2, Line 37, the pH value should read -- 5.7 -- instead of -- 5, 7 --

Signed and Sealed this
Twenty-second Day of September, 2020

Andrei Iancu
*Director of the United States Patent and Trademark Office*